US009653784B2

(12) United States Patent
Converse et al.

(10) Patent No.: US 9,653,784 B2
(45) Date of Patent: May 16, 2017

(54) CONFORMAL, WEARABLE, THIN MICROWAVE ANTENNA FOR SUB-SKIN AND SKIN SURFACE MONITORING

(71) Applicant: Lawrence Livermore National Security, LLC, Livermore, CA (US)

(72) Inventors: Mark C. Converse, Livermore, CA (US); John T. Chang, Danville, CA (US); Eric B. Duoss, Dublin, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 258 days.

(21) Appl. No.: 13/787,349

(22) Filed: Mar. 6, 2013

(65) Prior Publication Data

US 2014/0253397 A1 Sep. 11, 2014

(51) Int. Cl.

| | |
|---|---|
| ***A61B 5/00*** | (2006.01) |
| ***H01Q 1/38*** | (2006.01) |
| ***H01Q 21/28*** | (2006.01) |
| ***H01Q 1/27*** | (2006.01) |
| ***H01Q 9/28*** | (2006.01) |

(52) U.S. Cl.

CPC ............... *H01Q 1/273* (2013.01); *H01Q 1/38* (2013.01); *H01Q 9/285* (2013.01); *H01Q 21/28* (2013.01); *Y10T 29/49016* (2015.01)

(58) Field of Classification Search

CPC .. H01Q 9/16; H01Q 1/12; H01Q 1/27; H01Q 1/38; H01Q 1/273; H01Q 9/285; H01Q 21/28; Y10T 29/49016; H01P 11/00

See application file for complete search history.

(56) References Cited

U.S. PATENT DOCUMENTS

| | | | | |
|---|---|---|---|---|
| 5,189,433 | A * | 2/1993 | Stern | H01Q 3/24 343/770 |
| 7,002,526 | B1 | 2/2006 | Adams et al. | |
| 7,193,573 | B2 | 3/2007 | Durso et al. | |
| 7,450,077 | B2 | 11/2008 | Waterhouse et al. | |
| 8,228,254 | B2 * | 7/2012 | Foltz et al. | 343/795 |
| 2006/0265034 | A1 * | 11/2006 | Aknine | A61N 1/40 607/101 |
| 2007/0276270 | A1 * | 11/2007 | Tran | A61B 5/0022 600/508 |
| 2011/0160549 | A1 * | 6/2011 | Saroka | A61B 5/00 600/301 |
| 2013/0082895 | A1 * | 4/2013 | Shiu et al. | 343/866 |
| 2013/0293429 | A1 * | 11/2013 | Keller et al. | 343/720 |
| 2014/0139385 | A1 * | 5/2014 | Yoon et al. | 343/745 |

* cited by examiner

*Primary Examiner* — Graham Smith
*Assistant Examiner* — Noel Maldonado
(74) *Attorney, Agent, or Firm* — Eddie E. Scott

(57) ABSTRACT

A wearable antenna is operably positioned on a wearer's skin and is operably connected the wearer's tissue. A first antenna matched to the wearer's tissue is operably positioned on the wearer's skin. A second antenna matched to the air is operably positioned on the wearer's skin. Transmission lines connect the first antenna and the second antenna.

14 Claims, 11 Drawing Sheets a=signal from transmitter b=% of signal a reflected from outer surface of skin c=a-b d=signal reflected form object of interest e=% of d reflected from inner surface of skin f=signal a minus b and c

CONFORMAL, WEARABLE, THIN MICROWAVE ANTENNA FOR SUB-SKIN AND SKIN SURFACE MONITORING

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present invention relates to antennas and more particularly to a conformal, wearable, thin microwave antenna for sub-skin and skin surface monitoring.

State of Technology

One of the biggest issues with non-invasive microwave monitoring of sub-skin tissue is the large reflection at the air/skin boundary. The present invention will act as a type of antenna relay across dissimilar boundaries increasing the signal passing through the air/skin interface and improving sub-skin monitoring capabilities. It will perform this function while being <1 mm thick, adhere to the skin surface and not require any auxiliary cables or ports, making it barely noticeable to the wearer.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a thin, conformal, wearable antenna operably positioned on a wearer's skin. The antennas basically act as relays across the skin/air interface, which is a high contrast dielectric interface. One antenna tuned is to the tissue and one is tuned to air. Transmission lines connect the first antenna and the second antenna.

The present invention has use in a variety of sub-surface sensing and is primarily designed for sub-skin sensing. Some uses are for monitoring vocal cord movement during speech, monitoring the airways during anesthesia, checking for brain hematomas, and monitoring a variety of biological processes such as heart rate and breathing rate in an unobtrusive manner. The antennas of the present invention are very small and thin, can attach directly to the skin without any cable coupling required.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 3 illustrates one example of a system constructed in accordance with the present invention.

DETAILED DESCRIPTION OF SPECIFIC EMBODIMENTS

Figure 1:
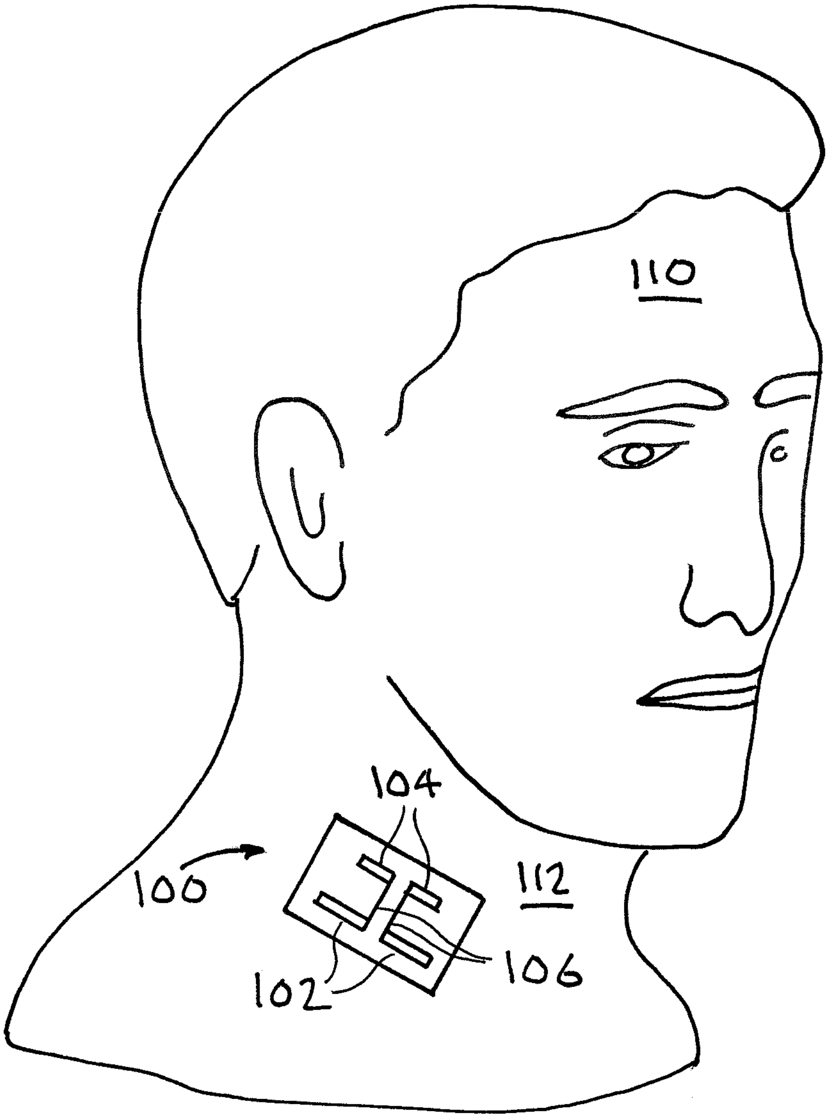
FIG. 1 is an illustration of one embodiment of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides a conformal sensor intended for microwave sensing and monitoring at the surface of or inside the body. The invention is suited for any situation where enhanced sensing is desired or where imaging across a high dielectric contrast boundary is desired. The present invention provides a thin, conformal, wearable antenna printed on a substrate which will adhere to the wearer's skin. The sensors can be attach to the surface of the skin, are conformal, and are less than 1 mm think and potentially <0.3 mm. The sensor consists of 2-3 linear flat strip antennas, co-planar lines, and in some cases a planar circulator. The antennas basically act as relays across the skin/air interface, which is a high contrast dielectric interface. One antenna tuned to the tissue and one tuned to air. The third antenna when used, works in conjunction with the circulator to rotate the polarization of the reflected signal which will increase device sensitivity. The present invention will compensate for reflections from the surface of skin (due to the high contrast interface) from a remote source of RF waves.

Referring now to the drawings and in particular to FIG. 1, one embodiment of the present invention is illustrated. The embodiment of the present invention is designated generally by the reference numeral 100. The embodiment 100 provides a wearable antenna mounted on the skin 112 of a wearer 110.

The embodiment of the present invention 100 is a thin, conformal, wearable antenna printed on a substrate which will adhere to the wearer's skin 112. The wearable antenna 100 is made up of a first antenna 102 and a second antenna 104 connected by co-planar transmission lines 106 on a substrate 108. The substrate 108 can be a silicone substrate. Alternatively, the substrate 108 can be a plastic substrate. The substrate 108 can be a polydimethylsiloxane (PDMS) substrate.

The first antenna 102 is a planar dipole antenna tuned to radiate into the air. The second antenna 104 is a planar dipole antenna tuned to radiate into tissue.

The embodiment of the present invention 100 provides an antenna system operably connected a wearer's tissue wherein the wearer's skin is exposed to air. A substrate 108 is adapted to be positioned on the wearer's skin 112. The first antenna 104 is matched to the wearer's tissue. The second antenna 102 is matched to the air. Transmission lines 106 connect the first antenna 102 and the second antenna 104.

Figure 2:
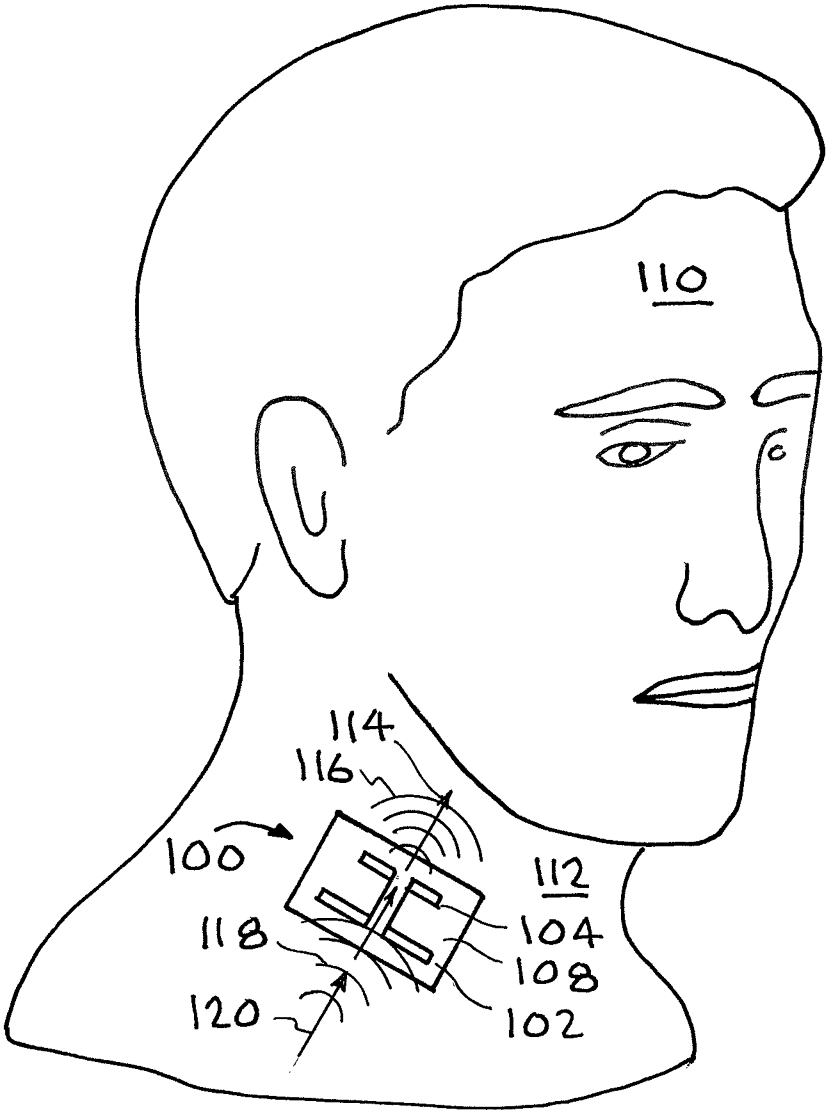
FIG. 2 provides additional details of the embodiment of the invention illustrated in FIG. 1.

Referring now to FIG. 2, additional details of the embodiment of the present invention 100 are illustrated. The embodiment 100 provides an antenna system operably connected a wearer's tissue wherein the wearer's skin is exposed to air. The substrate 108 is positioned on the wearer's skin 112. The first antenna 104 is matched to the wearer's tissue 114. The second antenna 102 is matched to the air 120.

As illustrated in FIG. 2, the first antenna 102 is a planar dipole antenna tuned to the air 120. The first antenna 102 receives radiated signals through the air 120 as indicated by the lines 118. The second antenna radiates the signals into the tissue 114 as indicated by the lines 116.

Figure 3:
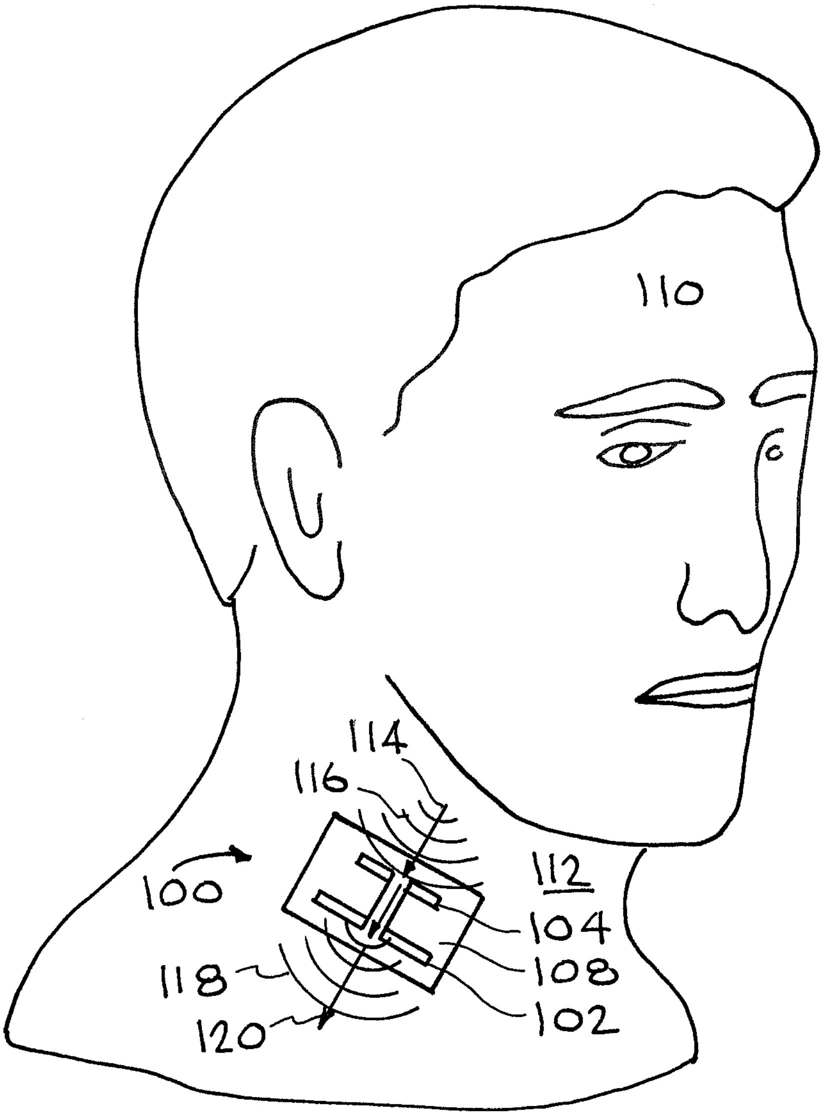
FIG. 3 provides additional information about the operation of the embodiment of the invention illustrated in FIG. 1.

Referring now to FIG. 3, additional details of the operation of the present invention 100 are illustrated. The second antenna 104 receives signals from the tissue 114 as indicated by the lines 116. The first antenna 102 radiates the signals into the air 120 as indicated by the lines 118.

The present invention is further described and illustrated by a number of examples of systems constructed in accordance with the present invention. Various changes and modifications of these examples will be apparent to those skilled in the art from the description of the examples and by practice of the invention. The scope of the invention is not intended to be limited to the particular examples disclosed and the invention covers all modifications, equivalents, and alternatives falling within the spirit and scope of the invention as defined by the claims.

Example 1

Two Antennas

Figure 4:
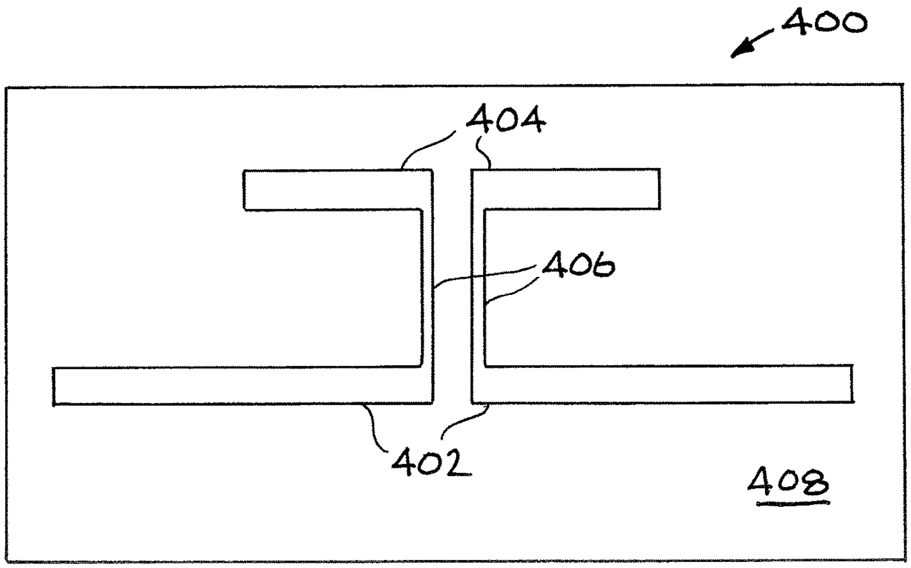
FIG. 4 illustrates another example of a system constructed in accordance with the present invention.

As illustrated in FIG. 4, an example of the present invention wherein a wearable antenna system utilizes two antennas. The two antenna system example is designated generally by the reference numeral 400. The wearable antenna 400 is a thin, conformal, wearable antenna printed on a substrate which will adhere to the wearer's skin. The wearable antenna 400 is made up of a first antenna 402 and a second antenna 404 connected by co-planar transmission lines 406 on a substrate 408. The first antenna 402 is a planar dipole antenna tuned to radiate into the air. The second antenna 404 is a planar dipole antenna tuned to radiate into tissue.

Example 2

Three Antennas

Figure 5:
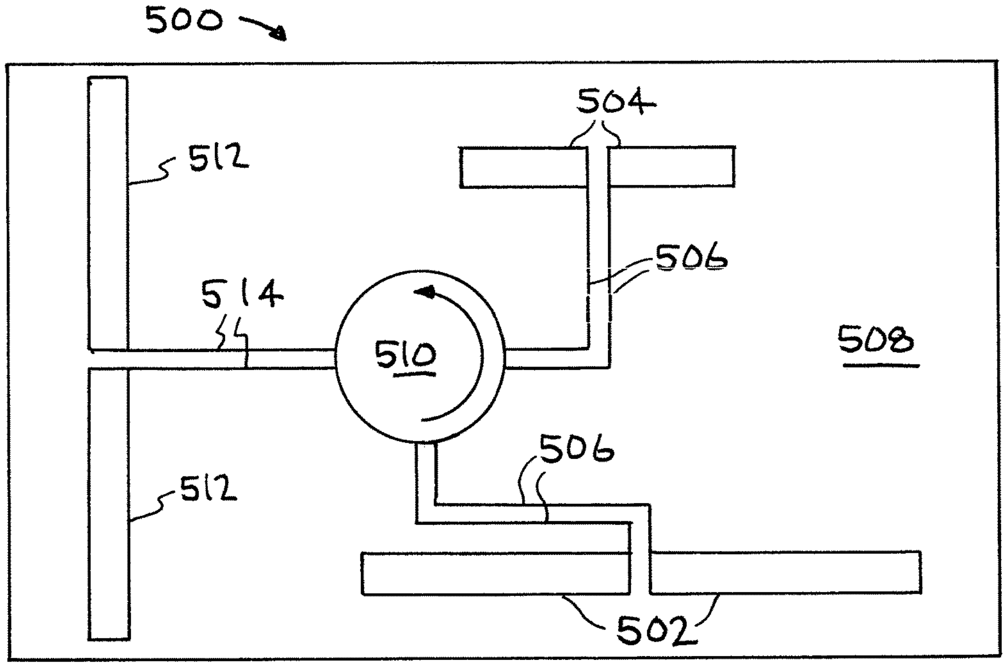
FIG. 5 illustrates yet another example of a system constructed in accordance with the present invention.

Referring now to FIG. 5, another embodiment of a thin, conformal, wearable antenna is illustrated. As illustrated in FIG. 5, an example of the present invention wherein a wearable antenna system utilizes three antennas. The three antenna system example is designated generally by the reference numeral 500. The three antenna system 500 consists of three planar dipole antennas 502, 504, & 512 printed onto a silicone (or other thin, flexible, and biocompatible) substrate 508, a planar circulator 510, all connected by coplanar lines 506 & 514 also printed onto the silicone substrate 508. In the three antenna system 500, the antennas 502, 504, & 512 are tuned to air or tissue. The antenna 502 is tuned to air and receives a signal radiated from an outside source. The signal propagates along the co-planar lines into circulator port 510, the signal leaves circulator port 510 and is radiated into the tissue from antenna 504. Any reflected signal enters circulator port 510 and exits circulator port 510 and is re-radiated from antenna 512 into the air to be picked up by a remote antenna. Due to the orientation of the dipoles the incoming signal from the remote source is orthogonal to any reflected signal picked up by antenna 504 from inside the tissue. This leads to greater sensitivity than other sensors due to the polarization difference between the input and output signal.

Example 3

Antennas on Same Side of Substrate

Figure 6:
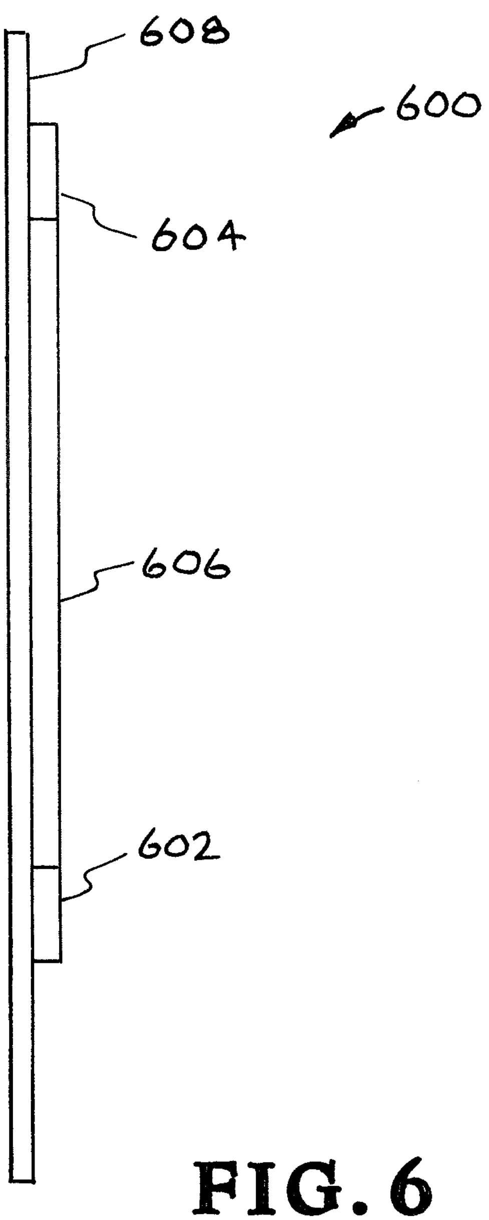
FIG. 6 illustrates another example of a system constructed in accordance with the present invention.

As illustrated in FIG. 6, an example of the present invention wherein a wearable antenna system utilizes antennas located on same side of a substrate. The system of example 3 is designated generally by the reference numeral 600. The wearable antenna 600 is a thin, conformal, wearable antenna printed on a substrate which will adhere to the wearer's skin. The wearable antenna 600 is made up of a first antenna 602 and a second antenna 604 located on the same side of the substrate 608. First antenna 602 and a second antenna 604 are connected by co-planar transmission lines 606 on the substrate 608. The first antenna 602 is a planar dipole antenna tuned to radiate into the air. The second antenna 604 is a planar dipole antenna tuned to radiate into tissue.

Example 4

Tattoo Antennas

Figure 7:
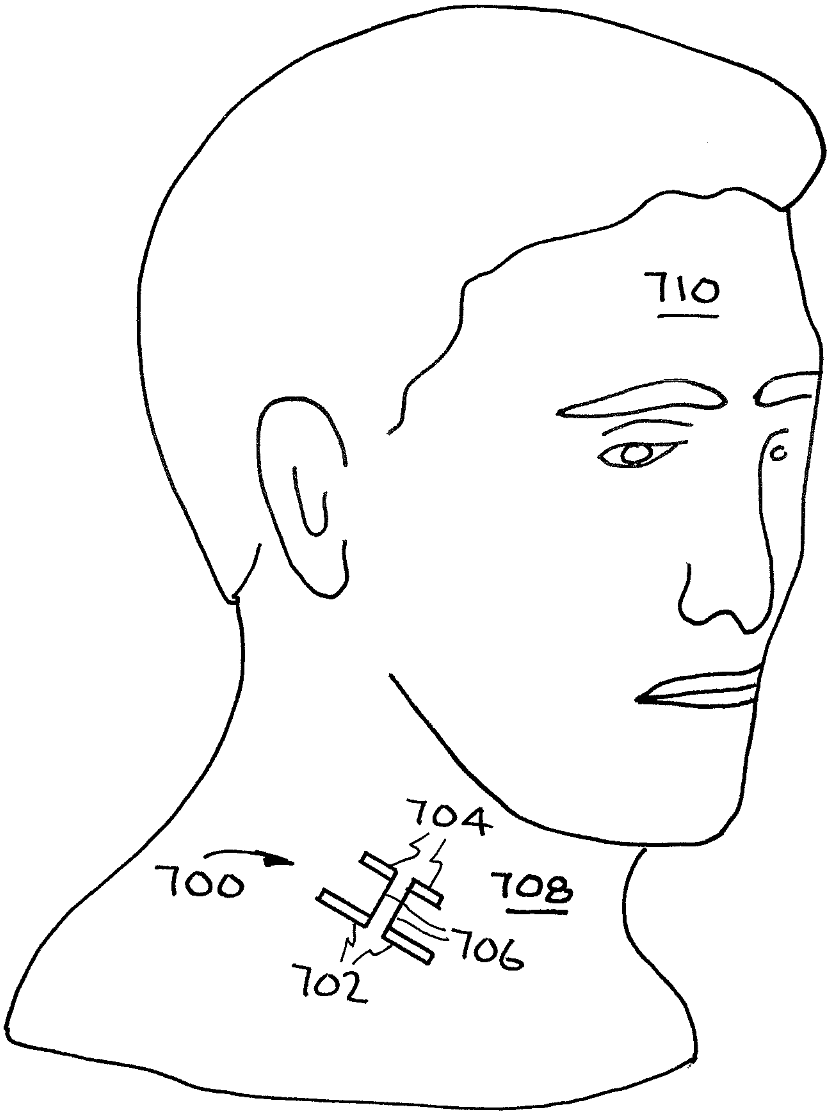
FIG. 7 illustrates an example of a system of the present invention wherein antennas are attached to the skin in the form of a temporary tattoo on a wearer's skin.

Referring now to FIG. 7, an example of the present invention is illustrated wherein a wearable antenna system is in the form of a temporary or permanent tattoo (or tattoos) on the skin. The embodiment of the present invention is designated generally by the reference numeral 700. The embodiment 700 provides a wearable antenna mounted on the skin 712 of a wearer 710 in the form of a temporary or permanent tattoo (or tattoos).

The wearable antenna 700 is made up of a first tattoo antenna 702 and a second tattoo antenna 704 connected by co-planar tattoo transmission lines 706 on the wearer's skin 708. The first antenna 702 is an antenna tuned to radiate into the air. The second antenna 704 is an antenna tuned to radiate into tissue.

The embodiment of the present invention 700 provides a tattoo antenna system operably connected a wearer's tissue wherein the wearer's skin is exposed to air. The first antenna 702 is a tattoo antenna matched to the wearer's tissue. The second antenna 704 is a tattoo antenna matched to the air. Tattoo transmission lines 706 connect the first antenna 702 and the second antenna 704.

Example 5

Monitoring Vocal Cord Movement

Figure 8:
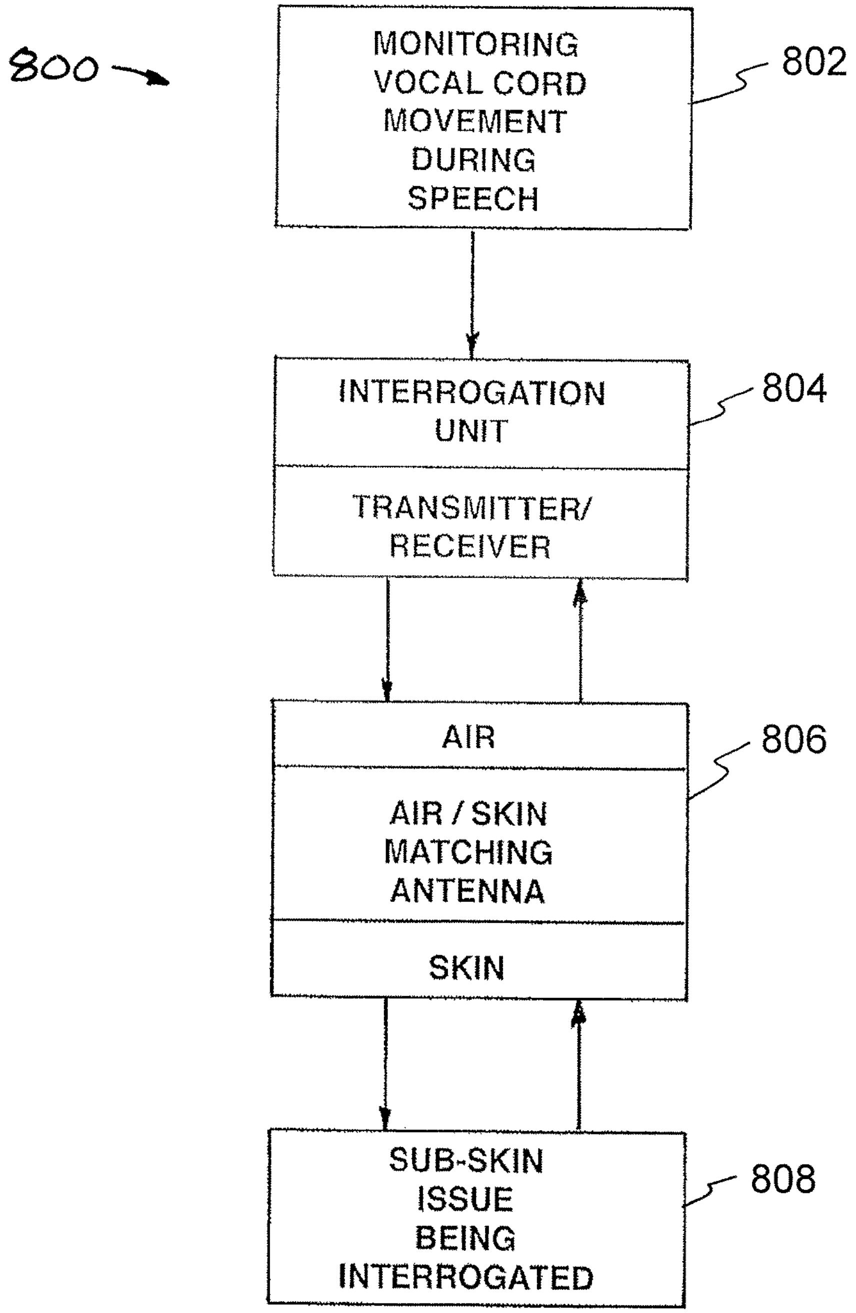
FIG. 8 illustrates a method of the present invention.

Referring now to FIG. 8, an example of the present invention for monitoring vocal cord movement during speech utilizing a wearable antenna is illustrated. The example is designated generally by the reference numeral 800.

The example 800 utilizes a wearable antenna mounted on the skin of a wearer for monitoring vocal cord movement during speech. The wearable antenna is made up of a first antenna and a second antenna connected by co-planar transmission lines. The first antenna is an antenna tuned to radiate into the air. The second antenna is an antenna tuned to radiate into tissue.

As shown in FIG. 8, the example 800 includes the following steps:

Step 802—This stage describes the monitoring of vocal cord movement during speech. A monitoring device and/or system consist of the electronic components and control interfaces that actuate and receive signals for the interrogation unit described in 804. The received signals and/or information gathered in step 802 includes the signal processing algorithms that transformed that signal into interpretable information pertaining to speech and voiced information.

Step 804—The interrogation unit receives command and control from the monitoring described in Step 802. It consists of the electronics that generates and receives the electromagnetic signals and is connected to one or more transmitting and receiving antenna into the conformal air/skin matching antenna as described in Step 806.

Step 806—The air/skin matching antenna consists of one or many physical structures composed of conductive and/or non-conductive materials that is electromagnetically matched to the signals transmitted by the interrogation unit of Step 804, and simultaneously and/or in stepwise layered fashion delivers energy into the human tissues or other materials.

Step 808—The energy or signal that is transferred from Step 806 is allowed to be positioned and directed towards sub-skin tissues and organs so that either an echo, scattered and/or transmitted signal can be subsequently be picked up by the same series of steps but in reversed order as described in Steps 808, 806, 804, and 802.

Example 6

Monitoring Airways During Anesthesia

Figure 9:
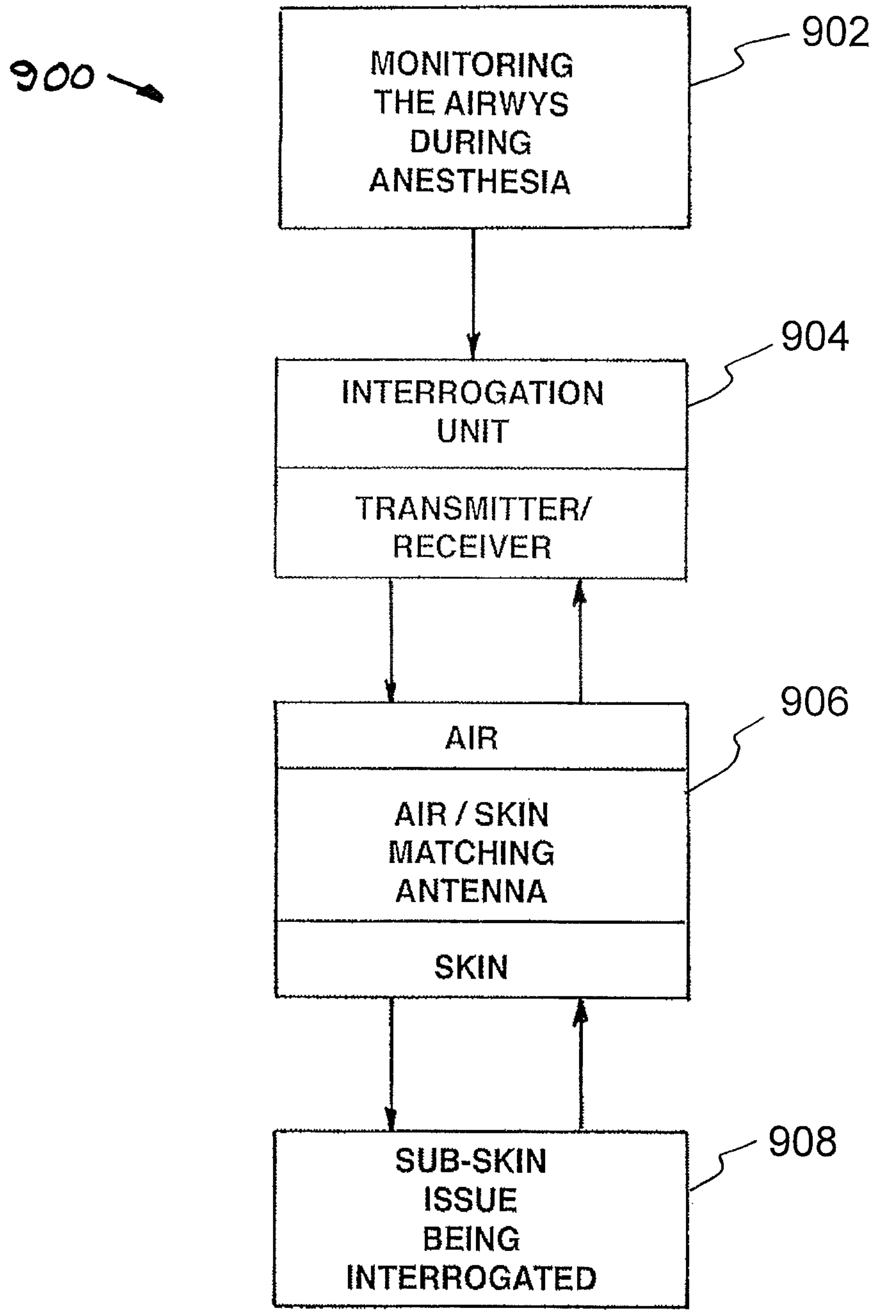
FIG. 9 illustrates another method of the present invention.

Referring now to FIG. 9, an example of the present invention for monitoring the airways during anesthesia utilizing a wearable antenna is illustrated. The example is designated generally by the reference numeral 900.

The example 900 utilizes a wearable antenna mounted on the skin of a wearer for monitoring the airways during anesthesia. The wearable antenna is made up of a first antenna and a second antenna connected by co-planar transmission lines. The first antenna is an antenna tuned to radiate into the air. The second antenna is an antenna tuned to radiate into tissue.

As shown in FIG. 9, the example 900 includes the following steps:

Step 902—This stage describes the monitoring of the airways during anesthesia. A monitoring device and/or system consisting of the electronic components and control interfaces that actuate and receive signals for the interrogation unit described in 904. The received signals and/or information gathered in step 902 include the signal processing algorithms that transformed that signals into interpretable information pertaining to the physical state of the airways.

Step 904—The interrogation unit receives command and control from the monitoring described in Step 902. It consists of the electronics that generate and receive the electromagnetic signals and is connected to one or more transmitting and receiving antenna into the conformal air/skin matching antenna as described in Step 906.

Step 906—The air/skin matching antenna consists of one or many physical structures composed of conductive and/or non-conductive materials that is electromagnetically matched to the signals transmitted by the interrogation unit of Step 904, and simultaneously and/or in stepwise layered fashion delivers energy into the human tissues or other materials.

Step 908—The energy or signal that is transferred from Step 906 is allowed to be positioned and directed towards sub-skin tissues and organs so that either an echo, scattered and/or transmitted signal can be subsequently be picked up by the same series of steps but in reversed order as described in Steps 908, 906, 904, and 902.

Example 7

Checking for Intracranial Bleeding and/or Hematoma

Figure 10:
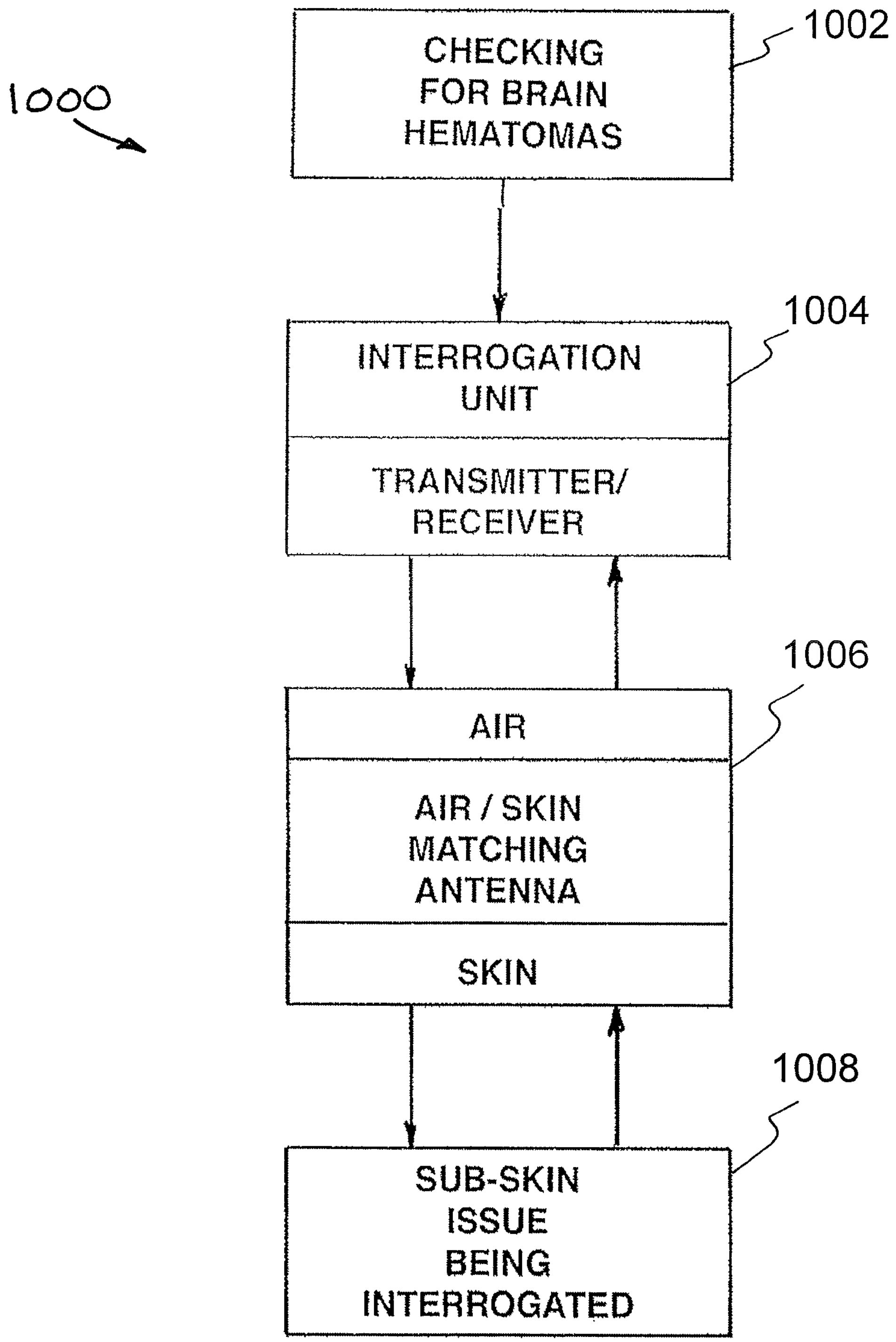
FIG. 10 illustrates yet another method of the present invention.

Referring now to FIG. 10, an example of the present invention for checking for brain hematomas utilizing a wearable antenna is illustrated. The example is designated generally by the reference numeral 1000.

The example 1000 utilizes a wearable antenna mounted on the skin of a wearer for checking for brain hematomas. The wearable antenna is made up of a first antenna and a second antenna connected by co-planar transmission lines. The first antenna is an antenna tuned to radiate into the air. The second antenna is an antenna tuned to radiate into tissue.

As shown in FIG. 10, the example 1000 includes the following steps:

Step 1002—This stage describes the monitoring and detection of intracranial bleeding. A monitoring and/or diagnostic device and/or system consisting of the electronic components and control interfaces that actuate and receive signals for the interrogation unit described in 1004. The received signals and/or information gathered in step 1002 include the signal processing algorithms that transformed that signals into interpretable information pertaining to the physical state of the airways. The signal and information obtained from a singular and/or pleural number of interrogation unit(s) and/or air/skin matching antenna(e) can also create images of the intracranial tissues.

Step 1004—The interrogation unit receives command and control from the monitoring described in Step 1002. It consists of the electronics that generate and receive the electromagnetic signals and is connected to one or more transmitting and receiving antenna into the conformal air/skin matching antenna as described in Step 1006.

Step 1006—The air/skin/tissue matching antenna consists of one or many physical structures composed of conductive and/or non-conductive materials that is electromagnetically matched to the signals transmitted by the interrogation unit of Step 1004, and simultaneously and/or in stepwise layered fashion delivers energy into the human tissues or other materials.

Step 1008—The energy or signal that is transferred from Step 1006 is allowed to be positioned and directed towards sub-skin tissues and organs so that either an echo, scattered and/or transmitted signal can be subsequently be picked up by the same series of steps but in reversed order as described in Steps 1008, 1006, 1004, and 1002.

Example 8

Monitoring Biological Processes

Figure 11:
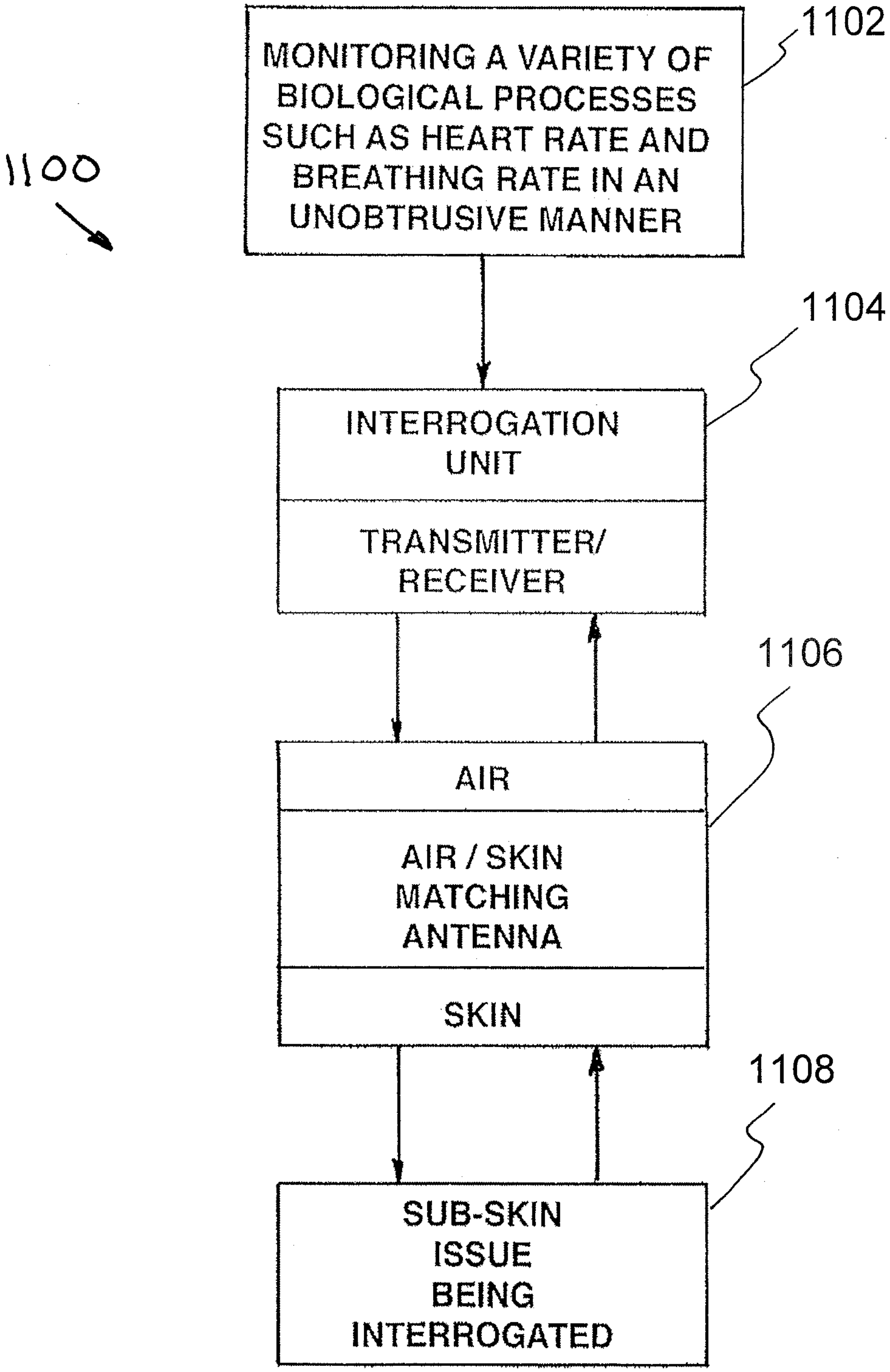
FIG. 11 illustrates a method of the present invention.

Referring now to FIG. 11, an example of the present invention for monitoring biological processes utilizing a wearable antenna is illustrated. The example is designated generally by the reference numeral 1100.

The example 1100 utilizes a wearable antenna mounted on the skin of a wearer for monitoring biological processes. The wearable antenna is made up of a first antenna and a second antenna connected by co-planar transmission lines. The first antenna is an antenna tuned to radiate into the air. The second antenna is an antenna tuned to radiate into tissue.

As shown in FIG. 11, the example 1100 includes the following steps:

Step 1102—This stage describes the monitoring general biological processes such as organs and tissues of humans and non-human animals. A monitoring device and/or system consist of the electronic components and control interfaces that actuates and received signals for the interrogation unit described in 1104. The received signals and/or information gathered in step 1102 include the signal processing algorithms that transformed that signals into interpretable information pertaining to the physical state of the airways.

Step 1104—The interrogation unit receives command and control from the monitoring described in Step 1102. It consists of the electronic that generates and receives the electromagnetic signals and is connected to one or more transmitting and receiving antenna into the conformal air/skin matching antenna as described in Step 1106.

Step 1106—The air/skin/tissue matching antenna consists of one or many physical structures composed of conductive and/or non-conductive materials that is electromagnetically matched to the signals transmitted by the interrogation unit of Step 1104, and simultaneously and/or in stepwise layered fashion delivers energy into the human tissues or other materials.

Step 1108—The energy or signal that is transferred from Step 1106 is allowed to be positioned and directed towards sub-skin tissues and organs so that either an echo, scattered and/or transmitted signal can be subsequently be picked up by the same series of steps but in reversed order as described in Steps 1108, 1106, 1104, and 1102.

Figure 12:
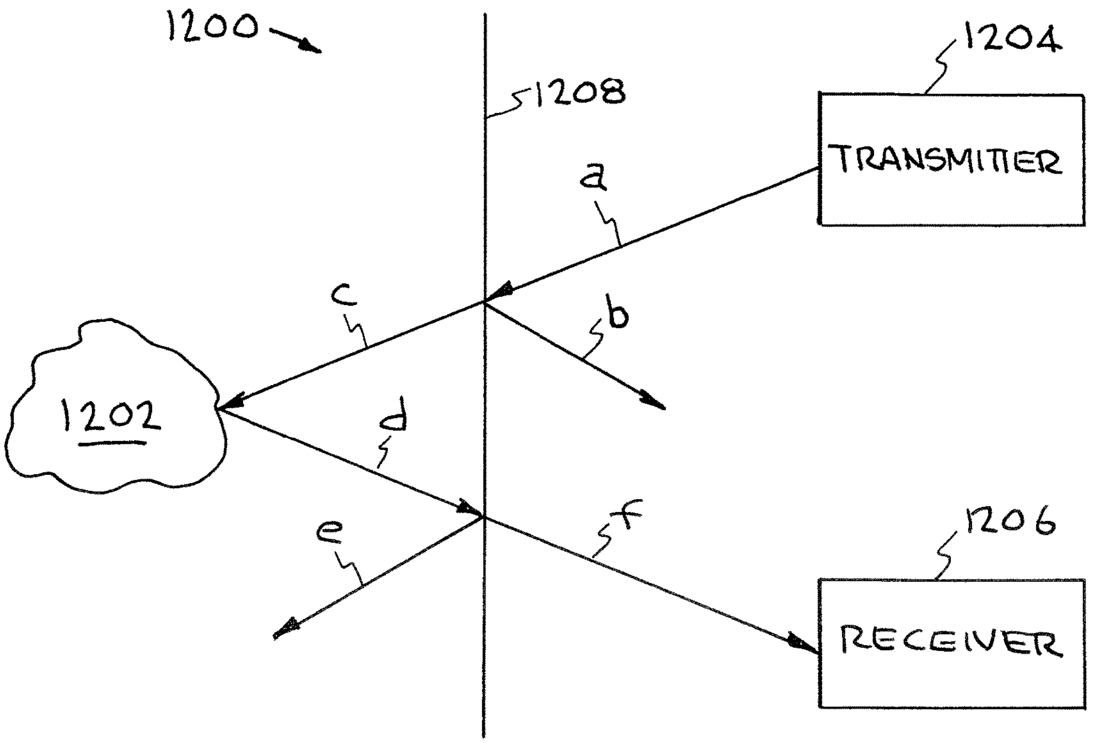
FIG. 12 is an illustration providing additional information about the present invention.

Referring now to FIG. 12, an illustration provides additional information about the present invention. The illustration is designated generally by the reference numeral 1200. The illustration 1200 utilizes a wearable antenna mounted on the skin of a wearer for monitoring biological processes. The wearable antenna is made up of a first antenna and a second antenna connected by co-planar transmission lines. The first antenna is an antenna tuned to radiate into the air. The second antenna is an antenna tuned to radiate into tissue. As shown in FIG. 12, the illustration depicts the operation of the device. In the absence of the device, the transmitter radiates a wave toward the skin a of magnitude A. A wave b of magnitude B is reflected from the surface. Wave c is the transmitted wave of magnitude C=A−B. Wave c interacts with the object of interest and some of that signal is reflected back toward the skin/air interface (d of magnitude D). Part of this wave (d) is reflected (e with magnitude E) from the skin surface interface, and part is transmitted (f with magnitude F), where F=D−E. Wave f is then read by the receiver.

In the presence of the device wave a of magnitude A is launched from the transmitter toward the surface. The wave interacts with antenna 1 which is tuned to air and a signal is picked up by the antenna of magnitude C' (where C'>C). This signal propagates through the coplanar waveguide and is radiated from the second antenna tuned to tissue. This wave c (with magnitude C'>C) interacts with the object of interest and some of that signal is reflected back toward the skin/air interface (d of magnitude D' where D'>D). This wave d is then picked up by antenna 2, propagates through the coplanar lines and is re-radiated from antenna 1 into the air as wave f (of magnitude F'>F). Wave f is then read by the receiver. Since F'>F, more signal is due to the object of interest is picked up by the receiver and overall signal loss due to reflections from the air tissue interface are reduced.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus directly attached to a wearer's skin and operably connected to the wearer's tissue that receives a signal from an outside source wherein the signal is radiated into the wearer's tissue, the wearer's sub-skin tissues, and organs and wherein a reflected signal is radiated and picked up by a remote antenna for sub-skin sensing and providing information about the physical state of the wearer's sub-skin tissues and organs, wherein the wearer's skin is exposed to air, comprising:

a flexible and biocompatible substrate directly attached to the wearer's skin;

co-planer lines on said substrate, a circulator port on said substrate connected to said co-planer lines;

a first antenna on said substrate connected to said co-planar lines and said circulator port that receives the signal from the outside source wherein said first antenna directs the signal to said co-planer lines and said circulator port;

a second antenna on said substrate connected to said co-planer lines and said circulator port wherein said second antenna receives the signal from said circulator port and wherein said second antenna transmits the signal into the wearer's tissue to the wearer's sub-skin tissues and organs and wherein the signal produces the reflected signal containing information about the physical state of the wearer's sub-skin tissues and organs from the wearer's sub-skin tissues and organs; and a third antenna on said substrate connected to said co-planar lines and said circulator port that receives the reflected signal containing information about the physical state of the wearer's sub-skin tissues and organs wherein said third antenna radiates the reflected signal into the air wherein it is picked up by the remote antenna.

2. The apparatus of claim 1 wherein said flexible and biocompatible substrate is made of polydimethylsiloxane.

3. An apparatus directly attached to a wearer's skin and operably connected to the wearer's tissue, the wearer's sub-skin tissues, and the wearer's organs for sub-skin sensing and providing information about the physical state of the wearer's sub-skin tissues and the wearer's organs, wherein the wearer's skin is exposed to air, comprising:

an outside source;

a signal produced by said outside source;

a remote antenna;

a flexible and biocompatible substrate directly attached to the wearer's skin;

a circulator port on said substrate;

transmission lines on said substrate, said transmission lines connected to said circulator port;

a first antenna on said substrate connected to said transmission lines and said circulator port that receives said signal from said outside source and directs said signal to said transmission lines and said circulator port;

a second antenna on said substrate connected to said transmission lines and said circulator port that receives said signal from said circulator port and transmit said signal into the wearer's tissue to the wearer's sub-skin tissues and the wearer's organs and produces a reflected signal containing information about the physical state of the wearer's sub-skin tissues and the wearer's organs from the wearer's sub-skin tissues and the wearer's organs; and a third antenna matched to the air and connected to said transmission lines and said circulator port, said third antenna positioned on said substrate wherein said third antenna receives said reflected signal and transmits said reflected signal containing information about the physical state of the wearer's sub-skin tissues and the wearer's organs through the air wherein it is picked up by said remote antenna for providing information about the physical state of the wearer's sub-skin tissues and the wearer's organs.

4. The apparatus of claim 3 wherein said transmission lines on said substrate are co-planar.

5. The apparatus of claim 3 wherein said transmission lines on said substrate are co-planar and are less than one millimeter thick.

6. The apparatus of claim 3 wherein said substrate is a plastic substrate.

7. The apparatus of claim 3 wherein said substrate is a polydimethylsiloxane substrate.

8. The ntenna apparatus of claim 3 wherein said first antenna is a planar dipole antenna printed onto a silicone substrate.

9. The apparatus of claim 3 wherein said third antenna matched to air is a planar dipole antenna.

10. The apparatus of claim 3 further comprising a dielectric filler between said transmission lines.

11. The apparatus of claim 3 further comprising a high dielectric constant, low loss filler between said transmission lines that will allow lower impedances and focus more fields between said transmission lines.

12. An apparatus directly attached to a wearer's skin and operably connected to a wearer's tissue, sub-skin tissues, and organs for obtaining interpretable information pertaining to speech and voiced information wherein the wearer's skin is exposed to air, comprising:

an outside source;

a signal produced by said outside source;

a remote antenna;

a polydimethylsiloxane substrate directly attached to the wearer's skin;

a circulator port on said substrate;

transmission lines on said substrate, said transmission lines connected to said circulator port;

a first antenna on said substrate and operably connected to said transmission lines and said circulator port that receives said signal from said outside source and directs said signal to said transmission lines and said circulator port;

a second antenna on said substrate connected to said transmission lines and said circulator port adapted to receive said signal from said circulator port and transmit said signal to the wearer's sub-skin tissues and the wearer's organs, said signal producing a reflected signal from the wearer's sub-skin tissues and the wearer's organs containing information about the physical state of the wearer's sub-skin tissues and the wearer's organs pertaining to speech and voiced information; and a third antenna matched to the air and connected to said transmission lines and said circulator port, said third antenna located on said substrate wherein said third antenna receives said reflected signal from the wearer's sub-skin tissues and organs containing information about the physical state of the wearer's sub-skin tissues and the wearer's organs pertaining to speech and voiced information from said circulator port and transmit said reflected signal containing information about the physical state of the wearer's sub-skin tissues and the wearer's organs pertaining to speech and voiced information through the air wherein it is picked up by said remote antenna for obtaining interpretable information pertaining to speech and voiced information.

13. A method of making an apparatus for obtaining information about the physical state of a wearer's sub-skin tissues and a wearer's organs, wherein the wearer's skin is exposed to air, comprising the steps of:

providing an outside source that produces a signal;

providing a remote antenna;

providing a flexible and biocompatible polydimethylsiloxane substrate;

positioning co-planer lines on said substrate, positioning a circulator port on said substrate connected to said co-planer lines;

positioning a first antenna on said substrate connected to said co-planar lines and said circulator port wherein said first antenna receives said signal from said outside source and transmits said signal through said co-planar lines to said circulator port;

positioning a second on said substrate connected to said co-planar lines and said circulator port wherein said first antenna receives said signal from said circulator port and transmit said signal to the wearer's sub-skin tissues and the wearer's organs wherein said signal produces a reflected signal containing information about the physical state of the wearer's sub-skin tissues and the wearer's organs, said second antenna matched to the wearer's tissue, providing a third antenna connected to said co-planar lines and said circulator port and matched to the air, positioning said third antenna on said substrate wherein said third antenna is adapted to receive said reflected signal and transmit said reflected signal containing information about the physical state of the wearer's sub-skin tissues and the wearer's organs into the air wherein it is picked up by said remote antenna;

attaching said substrate directly onto the wearer's skin, and monitoring said reflected signal containing information about the physical state of the wearer's sub-skin tissues and the wearer's organs from said third antenna that is picked up by the remote antenna for providing information about the physical state of the wearer's sub-skin tissues and the wearer's organs.

14. A method of providing information about the physical state of a wearer's sub-skin tissues and a wearer's organs wherein the wearer's skin is exposed to air, comprising the steps of:

providing an outside source that produces a signal;

providing a remote antenna;

providing a flexible and biocompatible polydimethylsiloxane substrate;

positioning co-planer lines on said substrate, positioning a circulator port on said substrate connected to said co-planer lines;

positioning a first antenna on said substrate connected to said co-planar lines and said circulator port wherein said first antenna is adapted to receive said signal from said outside source and transmit said signal through the co-planar lines to said circulator port;

positioning a second antenna on said substrate connected to said co-planar lines and said circulator port wherein said second antenna is adapted to receive said signal from said co-planar lines and said circulator port and to transmit said signal to the wearer's sub-skin tissues and the wearer's organs, said second antenna matched to the wearer's tissue wherein said signal produces a reflected signal containing information about the physical state of the wearer's sub-skin tissues and the wearer's organs from the wearer's sub-skin tissues and the wearer's organs;

providing a third antenna connected to said co-planar lines and said circulator port and matched to the air;

positioning said third antenna on said substrate to receive said reflected signal containing information about the physical state of the wearer's sub-skin tissues and the wearer's organs, and transmit said reflected signal into the air wherein it is picked up by a said remote antenna;

attaching said substrate directly to the wearer's skin, and providing a monitoring device adapted to receive said reflected signal containing information about the physical state of the wearer's sub-skin tissues and the wearer's organs from said remote antenna for providing information about the physical state of the wearer's sub-skin tissues and the wearer's organs.

* * * * *